United States Patent [19]
Eickhorst

[11] 3,989,379
[45] Nov. 2, 1976

[54] APPARATUS FOR THE SPECTROSCOPICAL EXAMINATION OF LIGHT TRANSMITTING OBJECTS SUCH AS PRECIOUS STONES

[76] Inventor: Manfred Eickhorst, Hans-Henny-Jahnn-Weg 21, 2 Hamburg 76, Germany

[22] Filed: May 27, 1975

[21] Appl. No.: 581,278

[30] Foreign Application Priority Data
May 27, 1974 Germany.................. 7418353[U]

[52] U.S. Cl. .................................................. 356/30
[51] Int. Cl.[2] ......................................... G01N 21/00
[58] Field of Search ............... 356/30, 31, 237, 239

[56] References Cited
UNITED STATES PATENTS

| | | | |
|---|---|---|---|
| 1,744,485 | 1/1930 | Michel et al. | 356/30 |
| 2,494,078 | 1/1950 | Woodruff | 356/30 |
| 3,610,756 | 10/1971 | Lenzen et al. | 356/30 |
| 3,751,162 | 8/1973 | Long | 356/30 |

*Primary Examiner*—Ronald J. Stern
*Assistant Examiner*—Richard A. Rosenberger
*Attorney, Agent, or Firm*—Beall & Jeffery

[57] ABSTRACT

Apparatus for the spectroscopical examination of light transmitting objects such as gems comprising a spectroscope unit, receptacle means for the gem provided with a light transmitting support, and a light source, the gem in the receptacle being situated at the point of intersection of the optical axes of the spectroscope and of the light source, the latter comprising a first overhead light source shining light onto the stone from above and a second, transillumination light source shining light through the stone, the angles between the optical axes of the spectroscope and the light sources being adjustable. The light emerging from the light sources is produced by a cold light projector and conducted to the light sources via fibre optics.

10 Claims, 2 Drawing Figures

3,989,379

APPARATUS FOR THE SPECTROSCOPICAL EXAMINATION OF LIGHT TRANSMITTING OBJECTS SUCH AS PRECIOUS STONES

BACKGROUND OF THE INVENTION

The invention relates to an apparatus for the spectroscopical examination of light transmitting objects such as precious stones (gem stones) comprising a spectroscope unit, receptacle means for the object to be examined, and a light source, the object of examination in its receptacle being situated at the point of intersection of the optical axes of the spectroscope and the light source. It is the function of such devices to investigate the spectral properties or precious stones in particular, that is to say, to determine the history and nature of a gem stone by means of its line or band spectrum.

Until now spectroscopes of various kinds have been employed for this purpose, with the help of which one observes by eye a light beam that has been firstly split up by a prism and then shone through the precious stone under examination.

There are different methods and arrangements of the apparatus that can be used in the spectroscopical examination of gem stones.

It is already known (see K. Schlossmacher, "Perlen und Edelsteine," 5th edition 1969, page 97 ff) to shine light through a gem stone when examining it. For this purpose an apparatus is provided in which the light source, the gem stone and the spectroscope are arranged in that order and practically on one optical axis. The disadvantage of this apparatus is that the intensity of the spectral lines is too weak because the light path in the object under examination is too short. More advantageous is the method that is at present most commonly used, in which the principle of reflection at the upper planar surface of the gem stone under examination is used. For this purpose devices are used (see Chudoba-Guebelin, "Edelsteinkundliches Handbuch," 3rd edition 1974, page 232 ff) in which the light is shone at an angle of 45° to the planar surface into the diamond, which is lying on its planar surface; the light is totally reflected and is then directed into a spectroscope, which is also angled at 45° to the planar surface. The disadvantage of this arrangement is that the angle setting of the spectroscope and of the light source is not adjustable, with the result that, when one is working with differing types of gems, that is to say with different optical properties (refractive index, reflective behaviour etc.), one must always use the same optical arrangement. Apart from the fact that, when using these devices, one works with only the reflected illumination from above, the fine adjustment of the optical axes of the light source and spectroscope results in a reduction of the intensity of the spectral lines, as is the case with the known transillumination device, described above.

Finally, one more spectroscope apparatus is known (see R. T. Liddicoat jr., Handbook of Gem Identification, 9th edition 1972, page 180 ff) in which the optical axis of the spectroscope is mounted so as to be pivotable with respect to the optical axis of the light source. With this device one works with the light from a lamp that has been shone through the precious stone under examination by means of a mirror system. The disadvantage of the transillumination system, which was explained in the previous paragraph, are, however, still present, despite of the fact that the pivotability of the spectroscope enables the device to be adapted to a certain extent to the optical properties of any particular precious stone.

BRIEF SUMMARY OF THE INVENTION

It is the object of the invention to produce a spectroscope device for the examination of light transmitting objects such as gems with which differing stones can be examined with confidence and precision, irrespective of their structure, their optical properties or how they have been ground.

According to the invention, the receptacle means are provided with a light transmitting support and the light source comprises both a first source shining light onto the stone from above also termed "overhead light source" and a second source shining light through the stone termed "transillumination light source", the angles between the optical axes of the spectroscope and of the light sources being adjustable.

The possibility is thus created of spectroscopically examining gem stones of totally different types under different sorts of illumination with one device, i.e., the stone may be examined under light from above, under light shone through the stone and, if necessary, under both types of illumination simultaneously. The spectroscope and light source can thus be easily adapted to suit the different optical properties of different stones.

The apparatus and method are particularly advantageous when, according to a further embodiment of the invention, the optical axis of the spectroscope is pivotable about its point of intersection with the optical axes of the overhead light source and of the transillumination light source, because the operator merely needs to pay attention to one adjustable element only. It can, however, also be advantageous when the optical axis of the overhead light source, too, is pivotable about the point of intersection of the optical axes, which makes a fine adjustment possible with regard to definite optical angle relationships in the gem and also a continuous adjustment of the light conditions within the stone once the spectroscope has been positioned.

In order to keep the apparatus as simple as possible to handle, small, and easy to pack, the spectroscope and overhead light source can, according to a further embodiment of the invention, be arranged on pivot means which have a common pivotal axis in its elongation passing through the point of intersection of the axes. These pivot means are preferably formed by angle brackets and can of course be moved independently of one another and without having to loosen any screws. They are, however, sufficiently tightly clamped so that the position of the spectroscope is not altered by the smallest vibration. The forming of the pivot means as angle brackets means that on these the spectroscope and overhead light source can be favourably and, above all, exchangeably mounted.

Should it be desired to provide the apparatus constructed in accordance with the invention with the spectroscope in a fixed position, for instance in a position which is particularly favourable for the operator, then, according to another form of the invention, the optical axes of both the overhead light source and the transillumination light source can be arranged to be pivotable about the point of intersection of the optical axes.

According to a further form of the invention the light emerging from the overhead light source and from the transillumination light source can be conducted to these sources by means of an overhead and a transillumination fibre optic respectively. Fibre optics of this type enable the light sources to be easily moved and adjusted, take up very little space and, in contrast to rigid light conductors, can be placed in those parts of the apparatus, between other components, that happen to be free.

At the same time the use of fibre optics produces another very significant advantage for the general and all-round application of spectroscope devices of this type, namely that the precious stone may be illuminated with cold light. For this purpose, according to a preferred embodiment of the invention, a small box-like housing carrying or containing the spectroscope unit, the receptacle means, the overhead light source, and the transillumination light source is provided with cold light projector means preferably provided with connections for first and second fibre optics conducting light to said overhead and transillumination light sources, respectively.

Finally, according to another embodiment of the invention, the receptacle means are stepped and downwardly tapering, that is to say, in the shape of an arena so that the gem stone under examination is always firmly supported, regardless of its size.

The advantages of the invention seen as a whole lie in the facts that the apparatus is basically very simply constructed, that it can be employed for widely differing types, shapes and sizes of gem stones, that it can be operated without difficulty and that it is clearly laid out and may be conveniently packed.

BRIEF DESCRIPTION OF THE DRAWINGS

Other and further objects of the present invention will be apparent from the following description and claims and are illustrated in the accompanying drawings which by the way of illustration show preferred embodiments of the present invention and the principles thereof and what now are considered to be the best modes contemplated for applying these principles. Other embodiments of the invention embodying the same or equivalent principles may be used and structural changes may be made as desired by those skilled in the art without departing from the present invention and the scope of the appended claims. In the drawings show:

Figure 1:
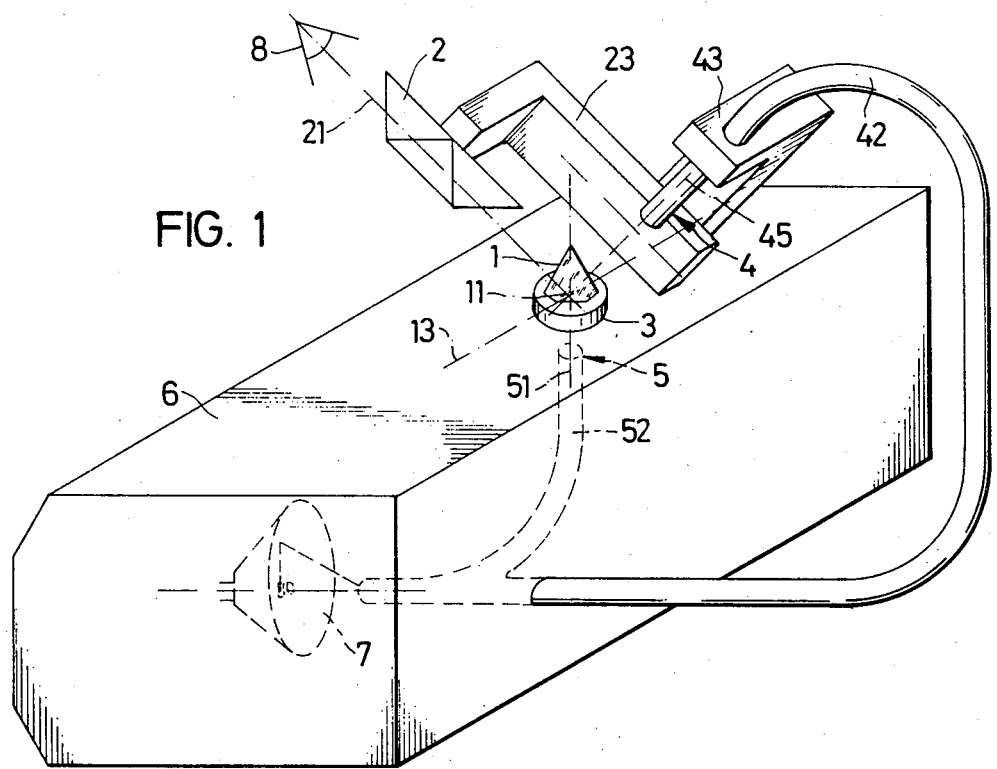
FIG. 1 an axonometric representation of the apparatus.
Figure 2:
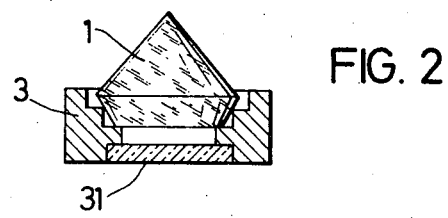
FIG. 2 an enlarged sectional view of the receptacle for the precious stone.

A gem stone 1 of brilliant-cut shape is positioned in a receptacle 3 which is provided with steps tapering downwardly and in its lower portion has a light transmitting plate 31. The receptacle 3 is preferably rotatably mounted on a box-like housing 6 and positioned in the operational area of a spectroscope 2, a first, i.e., an overhead light source 4 and a second, i.e., transillumination light source 5. The spectroscope 2, in the form of a spectroscope unit, is pivotably mounted on the housing 6 by means of a spectroscope pivot-arm 23, which is formed as an angle bracket. The overhead light source 4 is similarly mounted by means of an overhead light pivot arm 43, which is also formed as an angle bracket. The overhead light source 4 is formed by a fibre optic light conductor, the overhead light conductor 42. The spectroscope pivot arm 23 and the overhead light source pivot arm 43 are pivotable about a common axis 13.

The transillumination source 5, which is situated in the housing 6 underneath the translucent plate 31, is also formed by a fibre optic light conductor, the transillumination light conductor 52.

The fibre optics 42 and 52 are connected to a cold light projector 7, positioned in the housing 6, and conduct the light produced by the projector into the gem 1.

The optical axis 21 of the spectroscope 2, the optical axis 41 of the overhead light source 4 and the optical axis 51 of the transillumination light source 5 have a common point of intersection 11, which is inside the gem 1. In order to ensure that this point of intersection 11 remains a common point of intersection when the angle brackets 23, 43 of the spectroscope 2 and/or of the overhead light source 4 are pivoted, the two pivot arms are pivotable about a common axis 13 which also goes through the point of intersection 11 of the optical axis 21, 41 and 51.

What I claim as my invention and desire to secure by Letters Patent is:

1. An apparatus for the spectroscopical examination of light transmitting objects such as precious stones comprising a spectroscope unit, receptacle means for the object to be examined, and a light source, the object of examination in the receptacle being situated at the point of intersection of the optical axes of the spectroscope and of the light source, wherein the receptacle means are provided with a light transmitting support and the light source comprising a first source shining light onto the stone from above and a second source shining light through the stone, the angles between the optical axes of the spectroscope and the light sources being adjustable.

2. Apparatus according to claim 1, wherein the optical axis of the spectroscope is pivotable about its point of intersection with the optical axes of the first light source and the second light source.

3. Apparatus according to claim 2, wherein the optical axis of the first light source is pivotable about the point of intersection of the optical axes.

4. Apparatus according to claim 3, wherein the spectroscope and the first light source are arranged on pivot means which have a common pivotal axis in its elongation passing through the point of intersection of the axes.

5. Apparatus according to claim 4, wherein the pivot means are formed by angle brackets.

6. Apparatus according to claim 1, wherein the optical axes of the first light source and the second light source are arranged to be pivotable about the point of intersection of the optical axes.

7. Apparatus according to claim 1, wherein the light of the first light source and of the second light source is conducted thereto by first and second fibre optics respectively.

8. Apparatus according to claim 1, wherein a small box-like housing carrying or containing the spectroscope unit, the receptacle means, the first light source and the second light source is provided with cold light projector means.

9. Apparatus according to claim 8, wherein the cold light projector means are provided with connections for first and second fibre optics conducting light to said first and second light sources respectively.

10. Apparatus according to claim 1, wherein the receptacle means are stepped and downwardly tapering.

* * * * *